United States Patent [19]

Malabarba et al.

[11] Patent Number: 4,914,187
[45] Date of Patent: Apr. 3, 1990

[54] ESTER DERIVATIVES OF ANTIBIOTIC L 17046

[75] Inventors: Adriano Malabarba, Milan; Paolo Strazzolini, Fiume Veneto; Ambrogio Magni, Osnago; Bruno Cavalleri; Aldo Trani, both of Milan, all of Italy

[73] Assignee: Gruppo Lepetit S.p.A, Gerenzano, Italy

[21] Appl. No.: 373,680

[22] Filed: Jun. 23, 1989

Related U.S. Application Data

[60] Continuation of Ser. No. 248,316, Sep. 19, 1988, abandoned, which is a continuation of Ser. No. 11,645, Feb. 4, 1987, abandoned, which is a division of Ser. No. 797,295, Nov. 12, 1985, Pat. No. 4,661,470.

[51] Int. Cl.$^4$ .............................................. C07K 5/12
[52] U.S. Cl. .................................................. 530/317
[58] Field of Search ........................................ 530/317

[56] References Cited

U.S. PATENT DOCUMENTS 4,534,969 8/1985 Phillips .

OTHER PUBLICATIONS

Synthetic Organic Chemistry, Ch. 14, pp. 480–481 (1953).

Primary Examiner—Lester L. Lee

[57] ABSTRACT

The present invention is directed to ester derivatives at the carboxylic function of the glycopeptidic antibiotic substance called antibiotic L 17046 with antimicrobial activity mainly against gram-positive bacteria.

5 Claims, No Drawings

ESTER DERIVATIVES OF ANTIBIOTIC L 17046

This is a continuation of application Ser. No. 248,316, filed Sept. 19, 1988, allowed Mar. 24, 1989 and now abandoned which is a continuation of application Ser. No. 011,645, filed Feb. 4, 1987, now abandoned, which is a divisional of application Ser. No. 797,295, filed Nov. 12, 1985, which issued on Apr. 28, 1987 as U.S. Pat. No. 4,661,470.

The present invention is directed to ester derivatives at the carboxylic function of the antibiotic substance called antibiotic L 17046 of the following formula I

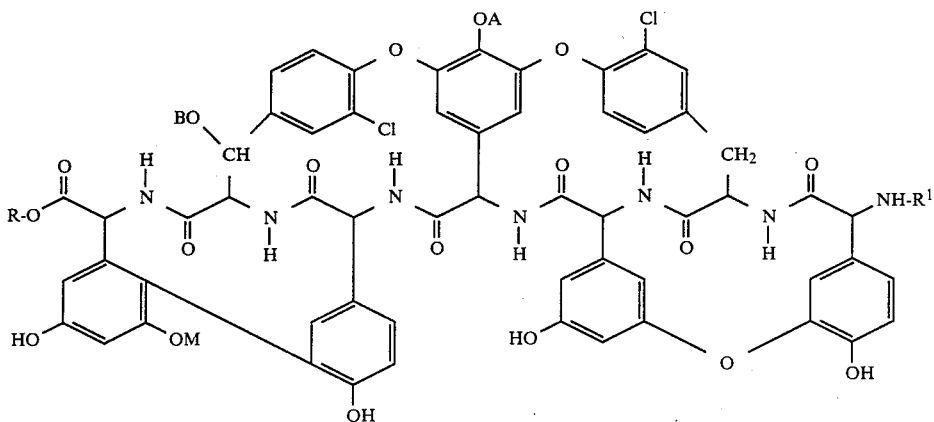

wherein

R represents $(C_1-C_{12})$alkyl, hydroxy$(C_1-C_{12})$alkyl, $(C_1-C_3)$alkoxy$(C_1-C_{12})$alkyl, halo$(C_1-C_{12})$alkyl, a group of formula $$H-[O(CH_2)_m]-_n$$

$$(C_1-C_3)alkyl[O(CH_2)_m]-_n$$

wherein m represents the integer 2 or 3, n is an integer from 1 to 10, and one of the hydrogen atoms of the $-(CH_2)-$group may be substituted by a methyl group; $(C_2-C_{10})$alkanoyloxymethyl, phenyl, substituted phenyl, phenyl$(C_1-C_6)$alkyl, substituted phenyl$(C_1-C_6)$alkyl, $R^1$ represents hydrogen or an amino-protecting group, A and M each represents a hydrogen atom, B is a N-acetyl-$\beta$-D-glucosaminyl group, and the pharmaceutically-acceptable acid addition salts thereof.

As used herein the term "alkyl" includes both straight and branched hydrocarbon groups; more particularly, "$(C_1-C_{12})$alkyl" represents a straight or branched aliphatic hydrocarbon chain of 1 to 12 carbon atoms such as methyl, ethyl, propyl, 1-methylethyl, butyl, 1-methylpropyl, 1,1-dimethylethyl, pentyl, 1-methylbutyl, 2-methylbutyl, 1-hexanyl, 2-hexanyl, 3-hexanyl, 3,3-dimethyl-1-butanyl, 4-methyl-1-pentanyl; 3-methyl-1-pentanyl, 2,2-dimethyl-3-pentanyl, 2,4-dimethyl-3-pentanyl, 4,4-dimethyl-2-pentanyl, 5-methyl-2-hexanyl, 1-heptanyl, 2-heptanyl, 5-methyl-1-hexanyl, 2-ethyl-1-hexanyl, 2-methyl-3-hexanyl, 1-octanyl, 2-octanyl, 2-cyclopentylethanyl, 1-nonanyl, 2-nonanyl, 1-decanyl, 2-decanyl and 3-decanyl, 1-undecyl, 2-dodecyl and the like, while "$(C_1-C_4)$alkyl" represents a straight or branched hydrocarbon chain of 1 to 4 carbon atoms; the term "$(C_1-C_3)$alkoxy" represents an alkoxy group of 1 to 3 carbon atoms, i.e. methoxy, ethoxy, n-propyloxy, isopropyloxy. The term "$(C_2-C_{10})$alkanoyloxymethyl" refers to alkanoyloxymethyl group wherein the alkanoyl portion is represented by a straight or branched alkanoyl group of 2 to 10 carbon atoms. Representative examples of $(C_2-C_{10})$alkanoyloxymethyl groups are: acetyloxymethyl, n-propionyloxymethyl, butyryloxymethyl, 2-methylpropanoyloxymethyl, pentanoyloxymethyl, 2-methylbutanoyloxymethyl, hexanoyloxymethyl, 3-methylpentanoyloxymethyl, 2,2-dimethylpropanoyloxymethyl, pivaloyloxymethyl, 3,3-dimethylbutanoyloxymethyl, 2,2-dimethylpentanoyloxymethyl, and the like. Examples of "5-7 membered aromatic, partially hydrogenated or saturated heterocycle ring" according to the invention are: pyrrolyl, pyridyl, pyrrolidinyl, pyridinyl, piperazinyl, imidazolyl, pyrimidinyl, pyridazyl, oxazolyl, oxazolidinyl, imidazolinyl, pyrazolidinyl, thiazolyl, thiazolinyl, thiazolidinyl, azepinyl, diazepinyl and thiazepinyl and the like. The term "halo$(C_1-C_{12})$alkyl" represents mono- or polyhalogenated alkyl group of 1 to 12 carbon atoms wherein the halo atom is chloro, fluoro or bromo Examples of halo$(C_1-C_{12})$alkyl groups are: monochloroethyl, dichloroethyl, trichloroethyl, dichlorofluoroethyl, difluorochloroethyl, difluoroethyl, trifluoroethyl, dichloropropyl, 1,1,1,3,3,3-hexafluoro-2-propyl, monochlorobutyl, difluorobutyl or trifluorobutyl and tetrafluorobutyl, and the like The term "$\beta$-poly-halo$(C_1-C_{12})$alkyl" refers in particular to halo$(C_1-C_{12})$alkyl derivatives having one or two halogen atoms in the position-8 of the alkyl chain. The term "substituted phenyl" indicates a phenyl residue which is substituted with one or two substituents selected from chloro, bromo, iodo, (C$-C_4$)alkyl, hydroxy, $(C_1-C_4)$alkoxy, $(C_1-C_4)$alkylthio, nitro, and trifluoromethyl. Examples of phenyl substituted alkyl groups are: benzyl, m-chlorobenzyl, o-fluorobenzyl, m-fluorobenzyl, p-fluorobenzyl, m-methylbenzyl, m-methoxybenzyl, o-ethoxybenzyl, m-butoxybenzyl, p-tert.butoxybenzyl, p-tert.butylbenzyl, phenethyl, p-chlorophenethyl, m-chlorophenethyl, o-methoxyphenethyl, m-methoxyphenethyl, o-propylphenethyl, o-ethoxyphenethyl, p-fluorophenethyl, p-bromophenethyl, o-propoxyphenethyl, o-butoxyphenethyl, 1-(p-isopropylphenyl)ethyl, 3-phenyl-1-propyl, 2-phenyl-1-propyl, 4-phenyl-1-butyl and 3-phenyl-1-butyl and the like.

The compounds of formula I possess a basic function which is capable of forming salts and therefore they can be transformed into their pharmaceutically acceptable acid-addition salts according to procedures known per se in the art. Generally, the salt form is preferred because of a better stability so that it can be easily stored. Representative and suitable acid addition salts of the compounds of formula I include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and like acids. The transformation of the free amino compounds of the invention into the corresponding acid addition salts, and the reverse, i.e. the transformation of an acid addition salt of a compound of the invention into the non-salt or free amino form, are within the ordinary technical skill and are encompassed by the present invention. In view of the similarity of the properties of the compounds of formula I and their salts, what is said in the present application when dealing with the biological activities of the compounds of formula I applies also to their pharmaceutically acceptable salts, and vice versa. The compounds of the invention are useful as semi-synthetic antibacterial agents or as intermediates to such agents. They are derivatives of the glycopeptidic antibiotic L 17046; more particularly, the compounds of the present invention are ester derivatives at the carboxy function of the antibiotic L 17046, N-protected antibiotic L 17046 or N-protected antibiotic L 17046 esters All these compounds possess antimicrobial activity; however, the N-protected antibiotic L 17046 and N-protected antibiotic L 17046 ester derivatives are mainly useful as intermediates to the antimicrobially active antibiotic L 17046 esters.

A preferred group of compounds of the invention is represented by those compounds of formula I wherein R represents $(C_1-C_4)$alkyl, hydroxy$(C_1-C_4)$alkyl, $(C_1-C_3)$alkoxy $(C_1-C_4)$alkyl, halo$(C_1-C_4)$alkyl, phenyl, phenyl substituted with one or two groups selected from chloro, bromo, iodo, (C )alkyl, hydroxy, $(C_1-C_4)$alkoxy and trifluoromethyl, phenyl$(C_1-C_4)$alkyl and substituted phenyl $(C_1-C_4)$alkyl wherein the phenyl group is substituted with one or two substituents selected from chloro, bromo, iodo, $(C_1-C_4)$alkyl, $(C_1-C_4)$alkoxy and trifluoromethyl, $R^1$, A, B and M are as defined above and the pharmaceutically acceptable acid addition salts thereof. Antibiotic L 17046 is disclosed in European Patent Application No. 84102665. It is prepared by controlled hydrolysis of teicoplanin, another known antibiotic substance which is described in U.S. Pat. 4,239,751.

Teicoplanin is the international non-proprietary name (INN) of the antibiotic substance formerly named teichomycin which is obtained by cultivating the strain *Actinoplanes teichomyceticus* nov.sp. ATCC 31121 in a culture medium containing assimilable sources of carbon, nitrogen and inorganic salts (see U.S. Pat. No. 4,239,751). According to the procedure described in the above cited patent an antibiotic complex containing Teichomycin $A_2$, $A_2$ and $A_3$ is recovered from the separated fermentation broth by extraction with a suitable water insoluble organic solvent and precipitation from the extracting solvent according to common procedures Teichomycin $A_2$, which is the major factor of the isolated antibiotic complex, is then separated from the other factors by means of column chromatography on Sephadex®. British Patent Application Publication No. 2121401 discloses that antibiotic Teichomycin $A_2$ actually is a mixture of five closely related co-produced main components According to recent structural studies it is possible to represent teicoplanin $A_2$ (formerly Teichomycin $A_2$) main components 1, 2, 3, 4 and 5 by the above formula I wherein R and $R^1$ are hydrogen, A is N—[$(C_{11}-C_{11})$aliphatic group,]-$\beta$-D-glucosaminyl group, B is a N-acetyl-$\beta$-D-glucosaminyl group and M is an u-D-mannosyl group. All these sugar moieties, when present, are linked to the teicoplanin nucleus through O-glycosidic bonds Representative and preferred examples of $(C_{10}-C_{11})$aliphatic acyl groups are n-decanoyl, 8-methylnonanoyl, Z-4-decenoyl, 8-methyldecanoyl, and 9-methyldecanoyl groups.

In addition, it has been found that it is possible to transform teicoplanin, a pure factor thereof or a mixture of any of said factors in any proportion, into unitary antibiotic products by means of selective hydrolysis of one or two sugar moieties. They are named antibiotic L 17054 and antibiotic L 17046, respectively.

Antibiotic L 17054 is represented by the above formula I wherein A, R and $R^1$ are hydrogen atoms, B is N-acetyl-$\beta$-D-glucosaminyl and M is $\alpha$-D-mannosyl wherein the sugar moieties are linked to the peptidic nucleus through an 0-glycosidic bond. It is described in European Patent Application No. 84102666.

Antibiotic L 17046 is represented by the above formula I wherein A, M, R and $R^1$ are hydrogen atoms, and B is N-acetyl-$\beta$-D-glucosaminyl wherein the sugar moiety is linked to the peptidic nucleus through an 0-glycosidic bond. It is described in European Patent Application No. 84102665. All the above named compounds, i.e. teicoplanin, a teicoplanin factor, a mixture of any said factors in any proportion, antibiotic L 17054 and antibiotic L 17046 are starting materials for the preparation of the ester derivatives of the invention.

To facilitate the discussion, in the present specification any one of the above starting materials, i.e. teicoplanin complex as obtained according to U.S. Pat. No. 4,239,751, any further purification thereof, a compound of the above formula I wherein R and $R^1$ are hydrogen, A represents hydrogen or a [$(C_{10}-C_{11})$aliphatic acyl]-$\beta$-D-glucosaminyl, B represents N-acetyl-$\beta$-D-glucosaminyl, and M represents hydrogen or $\alpha$-D-mannosyl with the proviso that when A is hydrogen also M is hydrogen, or any mixture thereof in any proportion will be generally referred to as a "teicoplanin-like compound" or a "teicoplanin-like substance".

The antibiotic L 17046 esters of formula I are prepared by submitting a suitable teicoplanin-like substance to esterification under controlled conditions These esterification conditions depend on the nature of the specific teicoplanin-like substance which is used as the starting material and, to a certain extent, on the specific ester which is desired. In general, the reaction conditions of the esterification procedure are such that the "teicoplanin nucleus" is not modified, and in case the substituents A and M of the starting teicoplanin-like substance are not all hydrogen atoms, the reaction conditions of the esterification procedure are such that these sugar moieties of the starting material are hydrolyzed before the main reaction is completed. Therefore, one object of the present invention is to provide a process for preparing a antibiotic L 17046 ester which comprises:

(a) submitting a teicoplanin-like substance, characterized by having a free or activated carboxylic acid function, to a controlled esterification procedure, and (b) when the starting material comprises a compound of formula I wherein at least one of A and M is a sugar moiety, providing a reaction medium capable of selectively hydrolyzing these sugar substituents without affecting either the remaining teicoplanin rest or the newly formed carboxylic acid ester function.

It will be recognized by those skilled in the art that the free aminic function of the teicoplanin-like substrates may interfere with the reaction course and therefore in some instances it will be necessary to protect this amino function before starting the esterification process. The N-protecting group which may be used in the process of the present invention is one of the N-protecting groups known in the art such as those described in reference books (see for instance T. W. Greene, "Protective Groups in Organic Synthesis", John Wiley and Sons, New York, 1981, p. 323-326, and M. Mc. Omie "Protecting Groups in Organic Chemistry", Plenum Press, New York, 1973) and which is capable of forming a bond with the amino groups of the teicoplanin-like derivative which is stable at the conditions of the reaction process, does not unfavourably interfere with the main esterification reaction, and is easily cleavable and removable from the reaction media at the end of the reaction process without altering the newly formed ester bond. Representative examples of N-protecting groups which may be advantageously used in the process of the invention are carbamate forming reagents characterized by the following oxycarbonyl groups: 1,1-dimethylpropynyloxycarbonyl, t-butyloxycarbonyl, vinyloxycarbonyl, allyloxycarbonyl, cinnamyloxycarbonyl, 4,5-diphenyl-3-oxazolin-2-one, benzyloxycarbonyl, p-nitrobenzyloxycarbonyl, 3,4-dimethoxy-6-nitrobenzyloxycarbonyl, 2,4-dichlorobenzyloxycarbonyl, 5-benzisoxazolylmethyloxycarbonyl, 9-anthrylmethyloxycarbonyl, diphenylmethyl oxycarbonyl, isonicotinyloxycarbonyl, S-benzyloxycarbonyl, and the like.

As it is appreciated by the skilled technician, the ultimate choice of the specific N-protecting group depends on the characteristics of the particular ester which is desired. In fact, this ester should be stable at the condition of removal of the N-protecting groups. Since the conditions of removal of the different N-protecting groups are known, the skilled technician is capable of selecting the proper protecting group. For instance, where a benzyl ester is desired, the N-protecting groups which are removable by catalytic hydrogenation, such as the benzyloxycarbonyl group, should be avoided, while those N-protecting groups which are removable under mild acidic conditions, such as t.butoxycarbonyl, can be conveniently used General procedures for preparing the compounds of the invention include therefore reacting a N-protected or free-amino teicoplanin-like substrate with an alcohol in an acidic medium, or a N-protected antibiotic L 17046 derivative with an alkyl halide (preferably bromide, chloride or iodide) as well as reacting a N-protected antibiotic L 17046 having an activated carboxylic function with the selected alcohol. The term "activated carboxylic function" means a derivatization of the carboxy function of the teico-planin-like substrate which renders this carboxy function reactive to coupling with the alcohol reactive to form the ester bond which characterizes the compounds of the invention. Representative examples of "activating agents" of the carboxylic function according to the invention, include carbonyldiimide derivatives, such as N,N'-dicyclohexylcarbodiimide, N,N'-diisopropylcarbodiimide and chlorinating agents of the carboxy function such as thionyl chloride. These agents which are capable of giving a reactive intermediate which, because of its instability, is in some instances not isolated, but conveniently reacted in situ with the selected alcohol to form the desired ester.

More particularly, controlled esterification procedures useful for preparing the antibiotic L 17046 ester derivatives of the invention include esterification reactions which employ acidic alcoholic conditions either in the presence of a N-protected teicoplanin-like derivative or preferably in the presence of a free teicoplanin-like derivative; esterification reactions wherein the teicoplanin-like substrate is treated with an excess of an acidic solution of the selected alcohol, which has to be a liquid at the reaction temperature; esterification reactions of a N-protected antibiotic L 17046 derivative with a suitable alcoholic substrate such as phenol or substituted phenol in the presence of a suitable activating agent of the carboxy function; and esterification procedures wherein an alkali metal, silver or lead salt of a N-protected antibiotic L 17046 derivative in an inert organic solvent is reacted with a halogenide of formula R-X, wherein R is as previously defined but with the exclusion of the halogenoalkyl groups, and X is a chlorine or preferably bromine or iodine atom, optionally in the presence of a tertiary amine such as triethylamine, picoline and the like.

A general procedure for preparing esters of formula I wherein the alcoholic residue is a residue of a alcohol which is a liquid at the reaction temperature and slightly water soluble or practically water insoluble, comprises, therefore, reacting a teicoplanin-like compound with a solution of the suitably selected alcohol in the presence of a mineral acid, preferably a hydrogen halide. The reaction temperature is preferably between 50° and 80° C. Preferred hydrogen halides are hydrogen bromide and hydrogen chloride with hydrogen chloride as the first choice. Representative examples of esters of formula I which can be prepared by this procedure are the $(C_1-C_{12})$alkyl, $(C_1-C_3)$alkoxy$(C_1-C_{12})$alkyl, halo(Cl-$C_1$-$C_2$)alkyl esters, phenyl$(C_1-C_{12})$alkyl, substituted phenyl $(C_1-C_{12})$alkyl esters, polyglycol esters having the alcoholic residue of formula

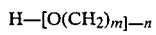

wherein m is as above and n is as above and polyoxyglycol monoalkylether esters having the alcoholic residue of formula

wherein m and n are as previously defined, with the proviso that, in the case of alkyl esters, the proximal carbon on the alkyl chain must not be a tertiary carbon. Any of the above listed teicoplanin-like compounds and any mixture thereof can be used as the starting material according to this procedure.

Representative examples of ester derivatives of formula I which can be prepared according to these methods are: L 17046 methyl, ethyl, n-propyl, i-propyl, n-butyl ester, L 17046 1-methylpropyl ester, L 17046 1,1-dimethylethyl ester, L 17046 pentyl ester, L 17046 1-methylbutyl ester, L 17046 2-methylbutyl ester, L 17046 1-hexanyl ester, L 17046 2-hexanyl ester, L 17046 3-hexanyl ester, L 17046 3,3-dimethyl-l-butanyl ester, L 17046 4-methyl-l-pentanyl ester; L 17046 3-methyl-l-pentanyl ester, L 17046 2,2-dimethyl-3-pentanyl ester, L 17046 2,4-dimethyl-3-pentanyl ester, L 17046 4,4-dimethyl-2-pentanyl ester, L 17046 5-methyl-2-hexanyl ester, L 17046 1-heptanyl ester, L 17046 2-heptanyl ester, L 17046 5-methyl-1-hexanyl ester, L 17046 2-ethyl-1-hexanyl ester, L 17046 2-methyl-3-hexanylester, L 17046 1-octanyl ester, L 17046 2-octanyl ester, L 17046 2-cyclopentylethanyl ester, L 17046 1-nonanyl ester, L 17046 2-nonanyl ester, L 17046 1-decanyl ester, L 17046 2-decanyl ester and L 17046 3-decanyl ester, L 17046 1-undecylester, L 17046 2-dodecyl ester, L 17046 benzyl ester, L 17046 m-chlorobenzyl ester, L 17046 o-fluorobenzyl ester, L 17046 m-fluorobenzyl ester, L 17046 p-fluorobenzyl ester, L 17046 m-methylbenzyl ester, L 17046 m-methoxybenzyl ester, L 17046 o-ethoxybenzyl ester, L 17046 m-butoxybenzyl ester, L 17046 p-tert.butoxybenzyl ester, L17046 p-tert.butylbenzyl ester, L 17046 phenethyl ester, L 17046 p-chlorophenethyl ester, L 17046 m-chlorophenetyl ester, L 17046 o-methoxyphenethyl ester, L 17046 m-methoxyphenethyl ester, L 17046 o-propylphenethyl ester, L 17046 o-ethoxyphenethyl ester, L 17046 p-fluorophenethyl ester, L 17046 p-bromophenethyl ester, L 17046 o-propoxyphenethyl ester, L 17046 o-butoxyphenethyl ester, L 17046 1-(p-isopropylphenyl)ethyl ester, L 17046 3-phenyl-l-propyl ester, L 17046 2-phenyl-l-propyl ester, L 17046 4-phenyl-l-butyl ester and L 17046 3-phenyl-l-butyl ester, L 17046 2-chloroethyl ester, L 17046 2-bromoethyl ester, L 17046 3-chloropropyl ester, L 17046 3-fluoropropyl ester, L 17046 4-bromobutyl ester, L 17046 4-fluorobutyl ester, L 17046 5-iodopentyl ester, L 17046 2-bromo-2-methylpropyl ester, L 17046 3-chloro-2-methylpropyl ester, L 17046 4-chloro-3-methylbutyl ester, and the acid addition salts thereof. A further general procedure for preparing the compounds of the invention, with the exception of those wherein R is a halogeno($C_1$–C12)alkyl group, phenyl and substituted phenyl group, comprises reacting a N-protected L 17046, either in the non-salt form and in the presence of a hydrogen halide acceptor or in the form of the alkali metal (K, Na), silver, lead salt, with a halogenide derivative of formula RX, wherein R is as above with the exclusion of halogeno(Cl- alkyl phenyl and substituted phenyl and X is chlorine or preferably bromine and iodine in an inert organic polar aprotic solvent. The reaction temperature is from about -5° C to 50° C. Preferably it is 15 to 50° C. The N-protected antibiotic L 17046 ester derivative is then N-deprotected according to the techniques outlined above or otherwise known in the art. Examples of suitable inert organic polar aprotic solvents are polar aprotic solvents such as dimethylformamide, dimethoxyethane, hexamethylphosphoramide, dimethylsulfoxide, benzene, toluene and the like. Examples of suitable hydrogen halide acceptors are tertiary organic amines such as triethylamine, picoline and the like as well as inorganic bases such as alkali metal bicarbonates, e.g. sodium or potassium bicarbonate. A preferred N-protecting group is in this case the tert.butoxycarbonyl group while a preferred inert organic polar aprotic solvent is dimethylformamide (DMF). The reaction time is generally between 24 and 50 h at about room temperature. Representative examples of the ester derivatives of formula I which can be prepared according to this method are: L 17046 methyl ester, L 17046 ethyl ester, L 17046 propyl ester, L 17046 1-methylethyl ester, L 17046 n-butyl ester, L 17046 1-methylpropyl ester, L 17046 1,1-dimethylethyl ester, L 17046 pentyl ester, L 17046 1-methylbutyl ester, L 17046 2-methylbutyl ester, L 17046 1-hexanyl ester, L 17046 2-hexanyl ester, L 17046 3-hexanyl ester, L 17046 3,3-dimethyl-l-butanyl ester, L 17046 4-methyl-l-pentanyl ester; L 17046 3-methyl-l-pentanyl ester, L 17046 2,2-dimethyl-3-pentanyl ester, L 17046 2,4-dimethyl-3-pentanyl ester, L 17046 4,4-dimethyl-2-pentanyl ester, L 17046 5-methyl-2-hexanyl ester, L 17046 1-heptanyl ester, L 17046 2-heptanyl ester, L 17046 5-methyl-l-hexanyl ester, L 17046 2-ethyl-l-hexanyl ester, L 17046 2-methyl-3-hexanylester, L 17046 1-octanyl ester, L 17046 2-octanyl ester, L 17046 2-cyclopentylethanyl ester, L 17046 1-nonanyl ester, L 17046 2-nonanyl ester, L 17046 1-decanyl ester, L 17046 2-decanyl ester and L 17046 3-decanyl ester, L 17046 1-undecylester, L 17046 2-dodecyl ester, L 17046 benzyl ester, L 17046 m-chlorobenzyl ester, L 17046 o-fluorobenzyl ester, L 17046 m-fluorobenzyl ester, L 17046 p-fluorobenzyl ester, L 17046 m-methylbenzyl ester, L 17046 m-methoxybenzyl ester, L 17046 o-ethoxybenzyl ester, L 17046 m-butoxybenzyl ester, L 17046 p-tert.butoxybenzyl ester, L 17046 p-tert.butylbenzyl ester, L 17046 phenethyl ester, L 17046 p-chlorophenethyl ester, L 17046 m-chlorophenetyl ester, L 17046 o-methoxyphenethyl ester, L 17046 m-methoxyphenethyl ester, L 17046 o-propylphenethyl ester, L 17046 o-ethoxyphenethyl ester, L 17046 p-fluorophenethyl ester, L 17046 p-bromophenethyl ester, L 17046 o-propoxyphenethyl ester, L 17046 o-butoxyphenethyl ester, L 17046 1-(p-isopropylphenyl)ethyl ester, L 17046 3-phenyl-l-propyl ester, L 17046 2-phenyl-l-propyl ester, L 17046 4-phenyl-l-butyl ester, L 17046 3-phenyl-l-butyl ester, and the acid addition salts thereof.

Still another procedure for preparing the compounds of the invention comprises reacting a carboxy activated N-protected L 17046 derivative with a suitable alcohol in an inert organic solvent. This procedure is particularly useful for preparing compounds of formula I wherein R is phenyl, substituted phenyl or β-(poly)-halogenoalkyl, and in general sterically hindered groups which are prepared with difficulties or in very low yields by the above described processes. According to this procedure, a N-protected L 17046 ester is obtained which can be deprotected according to known per se techniques. Also the "activation" step of the N-protected L 17046 derivative is obtained according to known per se techniques as described above and known in the art. Alternatively the N-protected L 17046 derivative and the suitable alcohol are dissolved in an inert organic solvent and the condensing agent, dissolved in the same solvent, is added thereto. In any case, the reaction temperature is generally between −15° C. and room temperature, preferably between −10° and 20° C. and most preferably between 0° C. and 15° C. Inert organic solvents are polar aprotic solvents as above defined while suitable condensing agents are as above described when dealing with the "activation" of the carboxy function of antibiotic L 17046. In addition to the known carbodiimide derivatives, also thionyl chloride is useful as activating agent of the carboxylic function. This activating agent is particularly preferred for preparing halo($C_1$–$C_{12}$)alkyl esters of formula I. Representative examples of the ester derivatives of formula I which can be prepared according to this method are: L 17046 phenyl ester, L 17046 4-chlorophenyl ester, L 17046 4-bromophenyl ester, L 17046 4-fluorophenyl ester, L 17046 3,4-dibromophenyl ester, L 17046 3,4-difluorophenyl ester, L 17046 3,4-dichlorophenyl ester, L 17046 3-bromo-4-chlorophenyl ester, L 17046 2,4-dichlorophenyl ester, L 17046 2,4-dibromophenyl ester, L 17046 2,4-difluorophenyl ester, L 17046 2,4,6-tribromophenyl ester, L 17046 2,4,6-trichlorophenyl ester, L 17046 4-methyl-2-chlorophenyl ester, L 17046 4-methyl-2-bromophenyl ester, L 17046 4-methoxy-2-chlorophenyl ester, L 17046 1-bromoethyl ester, L 17046 1,1-dichloroethyl ester, deglucoteicoplanin 1-fluoroethyl ester, L 17046 1,1-difluoroethyl ester, L 17046 1-bromo-2-chloroethyl ester, L 17046 1,1-dichloropropyl ester, L 17046 1-chloro-1-methylethyl ester, L 17046 1,1-dichloro-2-methylpropyl ester, L 17046 1-bromo-2-methylpropyl ester, L 17046 1,1,1-trifluoromethyl ester, L 17046 1-chloromethyl ester; the N-protected intermediates to such compounds and the acid addition salts thereof.

Some chloroalkyl esters, namely the 3-chloropropyl, 4-chlorobutyl, 5-chloropentyl, 6-chlorohexyl, 4-chloropentyl, 4-chloro-3-methylbutyl, and 5-chloro-4-methylpentyl esters may be prepared also by reacting antibiotic L 17046 respectively with oxetane, tetrahydrofurane, tetrahydropyrane, oxepane, 2-methyl-tetrahydrofurane, 3-methyl-tetrahydrofurane, 3-methyltetrahydropyrane in the presence of bubbling hydrogen chloride. The reaction temperature is preferebly between 30 and 60° C. The reaction is generally completed in 4-24 h. It will be recognized by those skilled in the art that the reaction time in the above reported esterification procedures varies depending on the specific reaction conditions and on the starting materials which are employed; however, since the compounds of the invention as well as the teicoplanin-like starting materials can be easily detected by autobioassay, TLC or HPLC methods, the skilled technician is also capable of monitoring the reaction course and determining when it is completed.

An example of the way in which the reaction course may be monitored by HPLC is as follows: samples of about 20 μl are drawn from the reaction mixture at predetermined times, diluted to a final concentration of about 2 mg/ml in a mixture 0.2% aqueous ammonium formate/acetonitrile, 50:50 (v/v) and injected into the HPLC system. The HPLC system is a chromatograph Varian 5000 equipped with 20 μl loop injector Rheodyne 7125; a UV detector at 254 nm and pre-column packed with Perisorb RP-8 Merck (30-40 μm) followed by a Hibar Merck column (25 cm) pre-packed with LiChrosorb RP-8 (10 μm).

Eluents: linear gradient from 15% B in A to 32% B in A in 20 min, at a flow rate of about 2 ml/min;
solution A: 0.2 % aqueous ammonium formate;
solution B: acetonitrile.

The relative retention times of some representative compounds of the invention in the above system are reported in Table Ia.

Another example of HPLC analytical procedure is the following:
samples of about 0.1 ml are drawn from the reaction mixture at predetermined times, diluted to a final concentration of about 0.7 mg/ml in a mixture 0.2% aqueous $NaH_2PO_4$/acetonitrile 50:50 (v/v) and infected into the HPLC system.

The HPLC system is a chromatograph Hewlett Packard 1084A.
Volume injected 20 1.

UV detector at 254 nm.
Column (25 cm) Hibar-Merck pre-packed with Lichrosorb
RP-8 (7 μm)
Eluents Solvent A: $NaH_2PO_4$ 0.02M/$CH_3CN$-25/75 (v/v) Solvent B: $NaH_2PO_4$ 0.02M/$CH_3CN$-95/5 (v/v)
Gradient t min 0, 2, 25, 30, 35, % B, 30, 30, 50, 60, 30.
Flow rate: 1.5 ml/min The relative retention times of some representative compounds of the invention in above system are reported in Table Ib.

It will be appreciated by those skilled in the art that the compounds of the invention can be prepared either from an essentially pure teicoplanin-like substance or from a crude teicoplanin-like substance.

In the former case, a compound of the invention can be obtained which may not need further particular purification step, while in the latter case a final purification step is necessary. Purification is generally obtained according to known per se techniques which includes: precipitation by non-solvents, extraction with solvents, salt formation, and chromatographic procedures. A preferred purification procedure involves the use of a reverse-phase column chromatography. A preferred adsorbent in this case is the silanized silica gel having a distribution particle range of 0.06-0.2 mm.

The eluent can be one of the hydrophilic mixtures that can be used in this purification technique. Representative examples of these hydrophilic eluents are the mixtures of diluted aqueous solution of ammonium salts of organic acids, acetonitrile or water soluble lower alkanols. Representative examples of diluted aqueous solutions of ammonium salts of organic acids are 0.1-6% ammonium formate aqueous solutions, while examples of suitable alkanols are methanol, ethanol, propanol and the like. Preferred eluents are a mixture of aqueous ammonium formate and acetonitrile at a pH between 6 and 8 or a mixture of aqueous ammonium formate and methanol.

A preferred procedure includes a first reverse phase chromatography on silanized silica gel (0.06-0.2 mm) developing with a linear step-gradient of 5 to 60% acetonitrile in 0.2% aqueous ammonium formate and a second column chromatography which uses a mixture of acetonitrile/water, 6:4 (v/v), as the eluent.

Another preferred procedure includes:
(a) contacting a solution of the crude antibiotic in 0.2% aqueous ammonium formate/methanol/butanol, 1:2:3, with silanized silica gel and stripping off the solvents,
(b) applying the residue at the top of a silanized silica gel (0.06-0.2 mm) column, developing with 0.6% aqueous ammonium formate and acetonitrile, 9:1, discarding the eluate and continuing the elution with a linear gradient of acetonitrile in water, obtained by mixing acetonitrile/water 1:9 and acetonitrile/water 7:3 at a rate of 200 ml/h.

The term "essentially pure" as referred to an antibiotic substance of the present disclosure, refers to substances having an HPLC titre greater than 95% (percent peak areas, at the pre-determined—254 nm—UV wavelength), a water and solvents content from 10% to 15% (by weight) and an inorganic residue lower than 0.5% (by weight).

The physico-chemical characteristics of representative compounds of the invention (the compounds of formula I wherein A and M represent independently hydrogen groups, B is N-acetyl-β-D-glucosaminyl and R and $R^1$ are as indicated in Table I below) are summarized in the following Tables Ia, Ib, II, III:

TABLE Ia

| Example No. | R | $R^1$ | $IR^{(c-1)(a)}$ ($\nu$ C=O ester) | $K^{(b)}$ | $pK_a^{(c)}$ |
|---|---|---|---|---|---|
| 1 | methyl | H | 1720 | 1.45 | 6.70 |
| 2 | ethyl | H | 1720 | 1.55 | 6.68 |
| 3 | n-butyl | H | 17150 | 1.95 | 6.65 |
| 4 | 2-chloroethyl | H | 1720 | 1.69 | 6.67 |
| 5 | 4-chloro-n-butyl | H | 1720 | 2.12 | 6.66 |
| 8 | benzyl | H | 1735 | | |
| 10 | (4-methyl)phenylmethyl | H | 1735 | | |
| 12 | 2-hydroxyethyl | H | 1740 | | |

$(a)$ registered in a nujol mull with a Perkin-Elmer 850 instrument $(b)$ $K = \dfrac{t_R \text{ ester}}{t_R / 17046}$ = relative retention time in the HPLC system described above $t_R$ L 17046 in this system $\approx$ 8.5 min.

$(c)$ the samples are dissolved in methylcellulose ®/water 4:1 (v/v), an excess of 0.01 M hydrogen chloride in the same mixture is added thereto and the resulting solution is titrated with 0.01 M NaOH in the same solvent mixture

TABLE Ib

| Example No. | R | $R_1$ | $K^k$ |
|---|---|---|---|
| 6 | Boc | H | 1 |
| 7 | Boc | 2-ethoxy-ethyl | 1.8 |
| 8 | H | 2-ethoxy-ethyl | 10.45 |
| 9 | Boc | benzyl | 2 |
| 10 | H | benzyl | 0.57 |
| 11 | Boc | p-methylbenzyl | 2.2 |
| 12 | H | p-methylbenzyl | 0.74 |
| 13 | Boc | 2-hydroxy-ethyl | 1.45 |

TABLE Ib-continued

| Example No. | R | $R_1$ | $K^k$ |
|---|---|---|---|
| 14 | H | 2-hydroxy-ethyl | 0.36 |

$K = \dfrac{t_R \text{ ester}}{t_R / 17046}$ $t_R$ L 17046 in this system $\approx$ 10.5 min.

TABLE II

| Example No. | UV ($\lambda$ max) (nm)* | | | |
|---|---|---|---|---|
| | Methanol | pH = 1.0 | pH = 7.4 | pH = 13.0 |
| 1 | 280 | 279 | 279 | 298 |
| 2 | 280 | 279 | 279 | 298 |
| 3 | 280 | 279 | 279 | 298 |
| 4 | 280 | 279 | 280 | 299 |
| 5 | 280 | 279 | 280 | 298 |

*recorded by means of a Unicam SP 800 spectrometer

TABLE III

ELEMENTAL ANALYSIS

| Example No. | Calcd. formula (MW) | C %$^a$ calcd. | C %$^a$ found | H %$^a$ calcd. | H %$^a$ found | N %$^a$ calcd. | N %$^a$ found | Cl % (total)$^b$ calcd. | Cl % (total)$^b$ found | Cl % (ionic)$^b$ calcd. | Cl % (ionic)$^b$ found | inorganic$^c$ residue % | weight$^d$ loss % |
|---|---|---|---|---|---|---|---|---|---|---|---|---|---|
| 1 | $C_{67}H_{60}N_8Cl_2O_{23}$·HCl (1452.5) | 55.40 | 55.08 | 4.57 | 4.63 | 7.71 | 7.30 | 7.32 | 7.35 | 2.44 | 2.46 | 0.2 | 3.7 |
| 2 | $C_{68}H_{62}N_8Cl_2O_{23}$·HCl (1466.7) | 55.69 | 55.25 | 4.33 | 4.42 | 7.64 | 7.44 | 7.25 | 7.41 | 2.42 | 2.53 | 0.2 | 3.9 |
| 3 | $C_{70}H_{66}N_8Cl_2O_{23}$·HCl (1494.7) | 56.24 | 56.03 | 4.52 | 4.71 | 7.50 | 7.36 | 7.12 | 7.35 | 2.37 | 2.51 | 0.5 | 5.3 |
| 4 | $C_{68}H_{61}N_8Cl_3O_{23}$·HCl (1501.1) | 54.41 | 54.28 | 4.16 | 4.30 | 7.47 | 7.29 | 9.45 | 9.71 | 2.36 | 2.62 | 0.2 | 12.9 |
| 5 | $C_{70}H_{65}N_8Cl_3O_{23}$·HCl (1529.2) | 55.44 | 55.46 | 4.35 | 4.45 | 7.33 | 7.12 | 9.27 | 9.45 | 2.32 | 2.47 | 0.2 | 4.8 |

$^a$ Determined on samples previously dried at 140° C. under nitrogen atmosphere
$^b$ Corrected for weight loss and inorganic residue
$^c$ Determined after heating the samples at 900° C. in oxygen atmosphere
$^d$ Determined by thermogravimetric analysis at 140° C.

The antibacterial activity of the compounds of the invention can be demonstrated in vitro by means of standard agar-dilution tests. Isosensitest broth (Oxoid) and Todd-Hewitt broth (Difco) are used for growing staphylococci and streptococci, respectively. Broth cultures are diluted so that the final inoculum is about $10^4$ colony forming units/ml (CFU/ml). Minimal inhibitory concentration (MIC) is considered as the lowest concentration which shows no visible growth after 18–24 h incubation at 37° C. The results of the antibacterial testing of representative compounds of formula I are summarized in table IV below:

TABLE IV

| MICROORGANISM | MIC ($\mu$g/ml) of the compounds of Example No. | | | | |
|---|---|---|---|---|---|
| | 1 | 2 | 3 | 4 | 5 |
| S. aureus ATCC 6538 | 0.125 | 0.25 | 0.25 | 0.25 | 0.25 |
| S. aureus TOUR ($10^3$ CFU/ml) | 0.125 | 0.25 | 0.125 | 0.25 | 0.125 |
| S. aureus TOUR ($10^6$ CFU/ml) | 0.5 | 0.5 | 0.25 | 0.5 | 0.125 |
| S. aureus TOUR + 30% bovine serum | 0.25 | 0.5 | 0.5 | 0.5 | 0.5 |
| S. epidermidis ATCC 12228 | 0.016 | 0.016 | 0.016 | 0.064 | 0.064 |
| S. pyogenes C 203 SKF 13400 | 0.5 | 0.5 | 0.25 | 0.25 | 0.25 |
| S. pneumoniae UC 41 | 0.5 | 0.5 | 0.5 | 0.5 | 0.125 |
| S. faecalis ATCC 7080 | 0.5 | 0.5 | 0.5 | 0.5 | 0.25 |
| E. coli SKF 12140 | 128 | 128 | 128 | 128 | 128 |

| MICROORGANISM | MIC ($\mu$g/ml) of the compounds of Example No. | | |
|---|---|---|---|
| | 8 | 10 | 12 |

TABLE IV-continued

| | | | |
|---|---|---|---|
| S. aureus TOUR ($10^3$ CFU/ml) | 0.125 | 0.125 | 0.125 |
| S. aureus TOUR ($10^6$ CFU/ml) | 0.125 | 0.25 | 0.125 |
| S. aureus TOUR + 30% bovine serum | 4 | 4 | 0.5 |
| S. epidermidis ATCC 12228 | 0.063 | 0.063 | 0.063 |
| S. pyogenes C 203 SKF 13400 | 0.125 | 0.125 | 0.25 |
| S. pneumoniae UC 41 | 0.25 | 0.5 | 1 |
| S. faecalis ATCC 7080 | 0.125 | 0.25 | 0.25 |
| E. coli SKF 12140 | 64 | 64 | 128 |

In addition to the antimicrobial activity against gram-positive bacteria, representative compounds of the invention possess a certain degree of activity against gram-negative bacteria.

In view of the above the compounds of the present invention can effectively be employed as the active ingredient of antimicrobial preparations used in human and veterinary medicine for the prevention and treatment of infectious diseases caused by pathogenic bacteria which are susceptible to said active ingredients. In such treatments, these compounds may be employed as such or also in the form of mixtures in any proportion. The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspension. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-liquid form. Topical applications may be formulated in hydrophobic or hydro-philic bases as ointments, creams, lotions, paints, or powders. Compositions for injection may take such forms as suspensions, solutions, or emulsions in oily or aqueous vehicles, and may contain formulatory agents such as suspending, stabilizing and/or dispersing agents. Alternatively, the active ingredient may be in powder form for reconstitution at the time of delivery with a suitable vehicle, such as sterile water. The amount of active principle to be administered depends on various factors such as the size and condition of the subject to be treated, the route and frequency of administration, and the causative agent involved. The compounds of the invention are generally effective at a daily dosage comprised between about 0.5 and about 30 mg of active ingredient per Kg of body weight, preferably divided in 2 to 4 administrations per day. Particularly desirable compositions are those prepared in the form of dosage units containing from about 20 to about 300 mg per unit. Representative examples of preparation of pharmaceutical compositions are as follows:

A parenteral solution is prepared with 100 mg of antibiotic L 17046 ethyl ester, hydrochloride dissolved in 2 ml of sterile water for injection A parenteral solution is prepared with 250 mg of antibiotic L 17046 butyl ester, hydrochloride dissolved in 3 ml of sterile water for injection A topical ointment is prepared with 200 mg of antibiotic L 17046 4-chloro-butyl ester, hydrochloride 3.6 g of polyethylene glycol 4000 U.S.P.

6.2 g of polyethylene glycol 400 U.S.P.

Besides their activity as medicaments, the compounds of the present invention can be used as animal growth promoters. For this purpose, one or more of the compounds of the invention is administered orally in a suitable feed. The exact concentration employed is that which is required to provide for the active agent in a growth promotant effective amount when normal amounts of feed are consumed. The addition of the active compounds of the invention to animal feed is preferably accomplished by preparing an appropriate feed premix containing the active compounds in an effective amount and incorporating the premix into the complete ration. Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and Co., S. Francisco, U.S A., 1969 or "Livestock Feeds and Feeding", 0 and B Books, Corvallis, Ore., USA, 1977) and are incorporated herein by reference. The following examples illustrate the manner in which the invention can be practiced, but, as such, should not be construed as limiting its overall scope.

PREPARATION OF THE STARTING MATERIALS

Preparation of antibiotic L 17054

5 g of teicoplanin is added to 60 ml of 0.5 N aqueous hydrochloric acid pre-heated to 80° C. with vigorous stirring. Stirring is continued and the temperature is maintained at about 80° C. for 30 minutes. Then, the mixture is rapidly filtered, the filtrate is cooled to 0-5° C. and 6 N hydrochloric acid (10 ml) is added. The resulting suspension is stirred for about 15 minutes while keeping the temperature at 0-5° C. The precipitate is collected, washed with 20 ml of cold 1 N HCl and then with ethyl ether, and dried under reduced pressure at room temperature resulting in crude antibiotic L 17054 hydrochloride (4.5 g).

Crude antibiotic L 17054 hydrochloride (3 g) as obtained above is suspended in a mixture of 0.2% aqueous $HCOONH_4/CH_3CN$ 95:5 (v/v) (150 ml). The pH is brought to about pH 7.5 with 1 N NaOH and the product is dissolved. The resulting solution is applied to a column containing 150 g of 0.06-0.2 mm silanized silica gel Merck prepared in the same solvent mixture. The column is developed with a linear gradient elution, from 5 to 21% of acetonitrile in 0.2% aqueous ammonium formate (v/v), collecting 20 ml fractions, which are monitored by HPLC. L 17054 containing fractions (70 to 96) are combined and the acetonitrile is removed under vacuum. The residual aqueous solution is applied to a column of 10 g of silanized silica gel in distilled water. After washing with distilled water until the salts are completely eliminated the product is eluted with a 1:1 (v/v) CH3CN:H2O mixture. The collected solution is concentrated under vacuum to a small volume and the antibiotic is precipitated by adding acetone. After drying at room temperature, 0.9 g of essentially pure antibiotic L 17054 is obtained.

Preparation of antibiotic L 17046

Teicoplanin (10 g) is added to 1 N hydrochloric acid (150 ml) preheated to 80° C. while stirring. After about 45 minutes the reaction mixture is cooled to 0-5° C. and 37% hydrochloric acid (~30 ml) is added. Stirring is maintained for about 10 minutes, after which the precipitated solid is recovered by filtration, washed with 20 ml of 2 N HCl, then with ethyl ether, and dried overnight over potassium hydroxide pellets at room temperature, resulting in crude antibiotic L 17046 hydrochloride (8.3 g).

The above crude product (6.2 g) is dissolved in 80% methanol (500 ml) and silica gel (30 g; Merck 0.06-0.2 mm) is added. After the addition of n-butanol (200 ml) the solvent is removed under vacuum. The residue is then applied to a silica gel chromatography column (300 g) in acetonitrile. The column is developed by using sequentially 300 ml each of the following solvent mixtures: acetonitrile, acetonitrile:water 95:5, acetonitrile:water, 90:10; acetonitrile:water, 85:15. The eluates are discarded and the column is developed with a linear gradient eluent obtained by mixing 3.5 l each of the following mixtures: acetonitrile:water, 83:17 and acetonitrile:water, 70:30 at a rate of 375 ml/h. Fractions of 25 ml each are collected and monitored by HPLC. The fractions which contain antibiotic L 17046 (fractions 170 to 200) are combined. n-Butanol (400 ml) is added to the pooled fractions and the resulting mixture is concentrated to a small volume. Acetone is then added to the cloudy solution and, after cooling to 10° C. a precipitate begins to form. After suitable time, the precipitation is complete and the solid is then collected by filtration, washed with acetone, then with ether, dried under vacuum at room temperature, yielding the compound of the title in essentially pure form (1.9 g).

EXAMPLE 1

Preparation of antibiotic L 17046 methyl ester, hydrochloride (a) from antibiotic L 17046

A stirred suspension of antibiotic L 17046 (3 g) in 90 ml of 0.35 M dry hydrogen chloride in 99.9% methanol is refluxed for about 2 hours (bath temperature about 80° C.). The reaction mixture is then cooled to 0°-5° C. and the precipitate collected, washed with diethyl ether (100 ml) and dried in vacuo at room temperature overnight, yielding 2.41 g of crude ester of the title. This crude product is suspended in 100 ml of water and the resulting suspension is brought to pH 8.3 with 0.1 N NaOH, then it is extracted with n-butanol (3×200 ml). The organic layers are pooled and 200 ml of water and 100 ml of ethyl acetate are added. The organic layer is then separated and concentrated in vacuo at 40° C. to a final volume of ~ 200 ml. By adding 200 ml of diethyl ether a solid separates which is collected, washed with 100 ml of diethyl ether and suspended in 50 ml of 99.9% methanol. The resulting suspension is refluxed (bath temperature ~80° C.) for 30 min then filtered hot. The filtrate is cooled to 15° C. and 1.6 ml of 10 M dry hydrogen chloride in 99.9 % methanol is added. On standing overnight at room temperature a solid separates which is collected, washed with a mixture of diethyl ether/acetone 3:1 (v/v) and dried at room temperature under vacuum for 8 hours yielding antibiotic L 17046 methyl ester, hydrochloride (1.93 g).

Essentially following the procedure of the foregoing Example 1 but substituting teicoplanin, teicoplanin A2 component 2, antibiotic L 17054 or any mixture thereof for antibiotic L 17046 as the starting material, the same compound of the title is obtained in similar yields (from 1.7 to 2.1 g, employing the same molar amount of reactant as in the foregoing Example).

EXAMPLE 2

Preparation of antibiotic L 17046 ethyl ester, hydrochloride (a) from antibiotic L 17046

To a stirred suspension of antibiotic L 17046 (3 g) in ethanol (112 ml), 8 ml of 4.5 M dry hydrogen chloride in ethanol is added. The reaction mixture is refluxed for 3 hours (bath temperature about 85° C.), then it is cooled to 5° C. and the precipitate is collected, washed with 5 ml of ethanol, then with 200 ml of diethyl ether and dried at room temperature under vacuum overnight, yielding 1.87 g of the crude ethyl ester of the title.

This crude product is dissolved in 180 ml of water and the resulting solution is brought to pH 8.9 with 0.1 N NaOH. A suspension forms which is extracted with 300 ml of a mixture of ethyl acetate/n-butanol 2:1 (v:v). The organic layer is discarded and the aqueous layer is extracted with 400 ml of n-butanol (2×200 ml). This organic extract is washed with water (60 ml) and concentrated at 45° C. in vacuo to a final volume of about 200 ml. By adding diethyl ether a solid separates which is collected, washed with 50 ml of diethyl ether and suspended in 50 ml of water. Then, 1 N hydrochloric acid (0.9 ml) is added and to the obtained clear solution n-butanol (200 ml) is added. The mixture is concentrated at 50° C. in vacuo to a final volume of about 60 ml. By adding diethyl ether (300 ml), a solid separates which is collected, washed with diethyl ether (100 ml) and suspended in 100 ml of 0.3 M dry hydrogen chloride in ethanol. The resulting suspension is concentrated at 35° C. in vacuo to a final volume of about 40 ml. The solid is collected, washed with 10 ml of ethanol, then with 200 ml of diethyl ether, yielding antibiotic L 17046 ethyl ester, hydrochloride (1.18 g)

(b) from antibiotic L 17054

A suspension of antibiotic L 17054 (2 g) in 100 ml of 0.6 M dry hydrogen chloride is absolute ethanol is refluxed for 3 hours (bath temperature about 80° C.), then it is cooled to about 5° C. and washed up as described in the foregoing examples 2a, yielding 0.58 g of the ethyl ester of the title.

Essentially following the procedure of the foregoing example 2b, but substituting teicoplanin or teicoplanin A2 component 2 for antibiotic L 17054 as the starting material, the compound of the title is obtained in similar yields (from about 0.4 to about 0.45 g, employing the same molar amount of reactants as in the foregoing Example).

EXAMPLE 3

Preparation of antibiotic L 17046 n-butyl ester, hydrochloride (a) from antibiotic L 17046

To a stirred suspension of antibiotic L 17046 (3 g) in 85 ml of n-butanol, 5.6 ml of butanolic 6.5 M hydrogen chloride is added at 60° C.. The clear solution which rapidly forms is stirred at about 60° C. for about 3 hours, then it is cooled to 5–10° C. and extracted with water (90 ml), after adjusting the pH of the aqueous layer to 8.2 (with 1 N NaOH). The organic layer is separated and diluted with 200 ml of n-butanol. The resulting cloudy butanolic solution is washed with 200 ml of water, then concentrated in vacuo at 50° C. to a final volume of ~80 ml. By adding 100 ml of ethyl acetate a solid separate which is collected and suspended in 250 ml of water. The suspension is stirred for about 30 minutes at room temperature, then 30 ml of methanol and 2 ml of 1 N hydrogen chloride are added. The resulting clear solution is brought to pH 8.1 with 0.1 N NaOH and extracted with acetate (400 ml). The organic layer is separated and discarded. The aqueous layer is extracted twice with 200 ml of n-butanol (2×200 ml) and to the collected organic layer 2 ml of 1N hydrochloric acid is added. The resulting butanolic solution is concentrated to a small volume (about 40 ml) in vacuo at 45° C. and by adding diethyl ether ( ~120 ml) a solid separates which is collected, washed with diethyl ether and dried under vacuum at 45° overnight, yielding antibiotic L 17046 n-butyl ester, hydrochloride (0.98 g).

Essentially following the procedure of the foregoing Example 3 but substituting teicoplanin, teicoplanin $A_2$ component 2, antibiotic L 17054 or any mixture thereof for antibiotic L 17046 as the starting material, the same compound of the title is obtained in similar yields (from 0.7 to 0.9 g, employing the same molar amount of reactants as in the foregoing Example).

EXAMPLE 4

Preparation of antibiotic L 17046 2-chloroethyl ester, hydrochloride from antibiotic L 17046

To a stirred suspension of antibiotic L 17046 (1.4 g) in 20 ml of 2-chloroethanol, 1 ml of thionyl chloride is added at −10° C. The reaction mixture is warmed to room temperature and stirred for one day. Then it is cooled to −10° C., thionyl chloride (1 ml) is added, and the mixture is stirred at room temperature for another day. The reaction mixture is then poured into diethyl ether (200 ml) and the solid which separates is collected, washed with diethyl ether and dried under vacuum overnight at room temperature, yielding 1.2 g of crude product 2-chloroethyl ester of the title. By working up this crude product as described in Example 2a for the purification of 1.87 g of crude antibiotic L 17046 ethyl ester, hydrochloride, 0.25 g of antibiotic L 17046 2-chloroethyl ester, hydrochloride is obtained.

EXAMPLE 5

Preparation of antibiotic L 17046 4-chlorobutyl ester, hydrochloride (a) from teicoplanin In a stirred suspension of teicoplanin (10 g) in dry tetrahydrofuran (200 ml), dry hydrogen chloride is bubbled for 12 hours, while maintaining the temperature at 45–50° C. The clear solution which forms is poured into 900 ml of diethyl ether, and the solid which separates is collected by filtration, washed with diethyl ether and dried under vacuum at room temperature overnight over KOH pellets, yielding 9.5 g of crude 4-dichlorobutyl ester of the title. This crude product is dissolved in 1.5 l of a mixture n-butanol/methanol/water 3:2:1 (v/v/v), 20 g of silanized silica gel (0.06–0.2 mm; Merck Inc.) is added and the solvents are stripped off in vacuo at about 45° C. The residue is suspended in 400 ml of acetonitrile/water 9:1 (v/v) and applied at the top of a chromatographic column prepared with 1.4 kg of the same silanized silica gel, pre-equilibrated with 1 l of 1% ammonium phosphate at pH 4.2 and stabilized with 200 ml of a mixture of acetonitrile/water 1:9 (v/v). The column is then washed with 1 l of acetonitrile/water 1:9, then developed with a linear gradient from 10% to 50% (v/v) of acetonitrile in water at a rate of 400 ml/h in 20 hours. Fractions of about 20 ml are collected and assayed by HPLC. Fractions containing antibiotic L 17046 4-chloro-n-butyl ester (241–320) are combined and after addition of n-butanol (2.5 l) and 1 N hydrogen chloride (4 ml) are concentrated to a small volume (~50 ml). The precipitate which forms by adding diethyl ether (~300 ml) is collected, washed with diethyl ether and dried under vacuum at room temperature overnight over KOH pellets and $P_2O_5$, yielding antibiotic L 17046 4-chloro-butyl ester, hydrochloride (2.1 g).

Essentially following the procedure of the foregoing Example 5a, but substituting teicoplanin $A_2$ component 2, antibiotic L 17054, antibiotic L 17046 or any mixture thereof for teicoplanin complex as the starting material, the same compound of the title is obtained with substantially the same yields (employing the same molar amount of reactant as in the foregoing Example).

EXAMPLE 6

Preparation of N-BOC derivative of antibiotic L 17046

To a stirred solution of L 17046 (3.8 g, 2.42 mMole) in distilled DMF (60 ml), 2,4,5-trichloro-t-butylcarbonate (1.02 g, 3,3 mMole) and triethylamine (2.12 ml) are added. The mixture is kept 48 hours at room temperature and the reaction end is checked by HPLC analysis. The reaction mass is then diluted with 240 ml of water, the pH is adjusted to 4 by adding N HCl and the mixture is extracted with n-butanol (300 ml in total). The organic phase is washed with 40 ml of water and concentrated under reduced pressure to a volume of about 40 ml of residue that is diluted with 300 ml of ether and cooled overnight. The solid which precipitates is collected by filtration, washed with ether and dried in vacuo at 50° C. Yield 4.2 g of pure compound of the title.

| Calc. % | C | 55.56 | H | 4.6 | N | 6.7 | Cl | 4.25 |
|---------|---|-------|---|-----|---|-----|-----|------|
| found % |   | 54.18 |   | 5.40 |   | 8.18 |    | 4.12 |

EXAMPLE 7

Preparation of benzyl ester of N-Boc antibiotic L 17046

N-BOC derivative of antibiotic L 17046 (500 mg, 0.333 mMole), KHCO3 (50 mg, 0,49 mMole) and benzyl bromide (80 μl, 0,66 mMole) are dissolved in 7 ml of distilled DMF and the reaction stirred at room temperature for 24 hours. The reaction mixture is diluted with 60 ml of water, the pH is brought to about 5 with acetic acid and the reaction product extracted twice with 50 ml of a mixture ethyl acetate/n-butanol 2:1. The organic layer is separated, washed with water (30 ml) and concentrated under reduced pressure to 10 ml that are diluted with 100 ml of ethyl ether. The solid which precipitates is collected by filtration, washed with ethyl ether and dried in vacuo overnight, yielding 450 mg of pure compound of the title.

EXAMPLE 8

Preparation of antibiotic L 17046 benzyl ester trifluoroacetate

The benzyl ester of N-BOC antibiotic L 17046 (450 mg) prepared by following the procedure of the foregoing Example 7 is dissolved in 2.5 ml of trifluoroacetic acid and stirred at room temperature for 15 minutes. The reaction mixture is diluted with ethyl ether (100 ml) and the solid which precipitates is collected, washed with ether and dried under vacuum at 50° C. overnight, yielding 400 mg of pure compound of the title.

| | C | H | N | Cl |
|---|---|---|---|---|
| Calc. % | 56.08 | 4.04 | 6.97 | 4.41 |
| Found % | 54.58 | 4.3 | 7.03 | 4.17 |

EXAMPLE 9

Preparation of 4-methylbenzyl ester of N-Boc antibiotic L 17046

A solution of N-BOC antibiotic L 17046 (500 mg, 0.333 mMole), KHCO3 (50 mg, 0.499 meq) and p-methylbenzyl chloride (90ul) in 7 ml of distilled DMF is stirred overnight at room temperature. Then a further portion of p-methylbenzyl chloride (90 μl ) and KHCO3 (20 mg) are added and the reaction mixture is kept at 50° C. for 7 hours and overnight at room temperature. The reaction mixture is diluted with 70 ml of water, the pH is adjusted to about 5 with acetic acid, then the mixture is extracted twice with 50 l of a mixture ethyl acetate/n-butanol 2:1. The organic layer is separated, washed with water (30 ml), and concentrated to a small volume at 50° C. The solid residue is triturated with diethyl ether (100 ml), collected, washed with diethyl ether and dried in vacuo at 50° C., yielding 480 mg of the compound of the title.

EXAMPLE 10

Preparation of antibiotic L 17046 (4-methyl)-benzyl ester 4-methylbenzyl ester of antibiotic L 17046 obtained according to example 9 (480 mg) is dissolved at room temperature in 2.5 ml of trifluoroacetic acid and this mixture is stirred for 15 minutes at room temperature. The reaction is quenched by dilution with 100 ml of diethyl ether and the solid is collected, washed with ether and dried in vacuo, yielding 420 mg of a crude material which is purified through flash chromatography on a column containing 70 g of LiChroprep RP C8-alkyl derivatized silica gel; 40–63 μm; Merck Co.) developed with a linear gradient from 25% to 50% of CH3CN in water. The fractions containing the pure derivative of the title are pooled, n-butanol is added and the solvents are evaporated under vacuum at 45° C. The residue is triturated with diethyl ether, then it is collected, washed with ether and dried in vacuo at 40° C., yielding 150 mg of pure title compound as free base.

EXAMPLE 11

Preparation of (2-hydroxy)ethyl ester of N-Boc antibiotic L 17046

A solution of N-BOC-antibiotic L 17046 (500 mg, 0.333 mMole), KHCO3 (50 mg) and 2-bromo-ethanol (50 μl) in 7 ml of distilled DMF is stirred at room temperature. Then, in a 98 hours period of time, several additions of the reactants are made for a total of 230 μl of 2-bromoethanol and 75 mg of KHCO (75 mg). The reaction is monitored by HPLC. The reaction mass is diluted with 70 ml of water, the pH is adjusted to about 5 by adding acetic acid and the mixture is extracted twice with n-butanol (50 ml). The organic layer is washed with water (30 ml) and it is concentrated under reduced pressure to 10 ml, then diethyl ether is added and the solid is collected, washed and dried in vacuo giving 450 mg of pure compound of the title.

EXAMPLE 12

Preparation of antibiotic L 17046 (2-hydroxy)ethyl ester trifluroacetate 2-(hydroxy)ethyl ester of antibiotic L 17046 (450 mg) prepared according to the procedure of example 11 is dissolved in 2.5 ml of trifluoroacetic acid and stirred 15 minutes at 20° C. then diethyl ether (100 ml) is added. The solid which precipitates is collected, washed with ether and dried in vacuo overnight at 50° C., yielding 390 mg of pure compound of the title.

We claim:

1. A process for preparing an antibiotic 1 17046 ester derivative of the following formula I

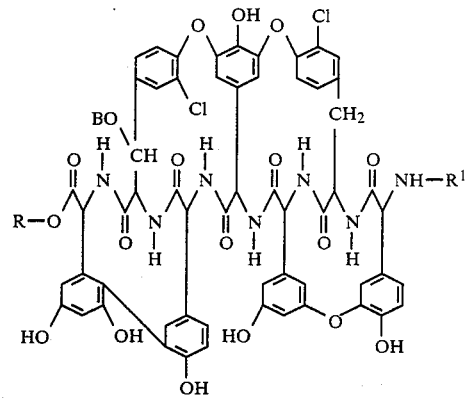

wherein R represents hydroxy (C1–C12)alkyl, (C1–C3)alkoxy(C1–C12)alkyl, a group of formula

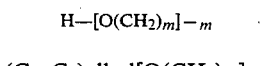

(C1–C3)alkyl[O(CH2)m]—n wherein m represents the integer 2 or 3, n is an integer from 1 to 10, and one of the hydrogen atoms of the —(CH2)— group may be substituted by a methyl group; (C2–C10)alkanoyloxymethyl, phenyl, substituted phenyl, phenyl (C1–C6)alkyl, substituted phenyl (C1–C6)alkyl; R1 represents hydrogen or an amino-projecting group, B is a N-acetyl-β-glucosaminyl group; and, the pharmaceutically-acceptable acid addition salts thereof, which comprises reacting a N-projected antibiotic L 17046 derivative with a compound of formula RX wherein R is as above and X represents a chlorine, bromine or iodine atom, in an inert organic polar paʳotic solvent, preferably in the presence of a hydrogen halide acceptor and at a temperature from about −5° C. and 50° C.

2. A process as claimed in claim 1 wherein the N-projected antibiotic L 17046 derivative is preferably an alkali metal, silver or lead salt of a N-protected antibiotic L 17046.

3. A process as claimed in claim 1 wherein the inert organic polar aprotic solvent is dimethylformaide.

4. A process according to claim 1, wherein the N-protecting group is tert-butoxycarbonyl.

5. A process for preparing an antibiotic L 17046 ester derivative of the following formula I

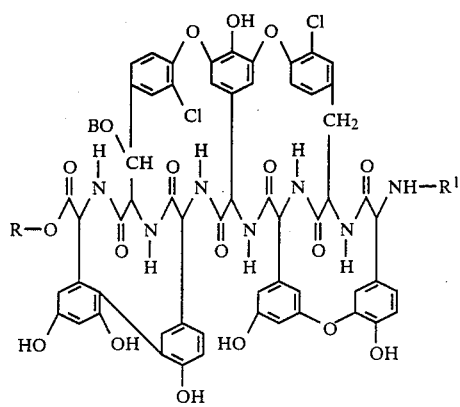

wherein R is selected from hydroxy($C_1$–$C_{12}$)alkyl, ($C_1$–$C_3$)alkoxy ($C_1$–$C_{12}$)alkyl, halo($C_1$–$C_{12}$)alkyl with the exclusion of β-poly-halo($C_1$–$C_{12}$)alkyl, phenyl(-$C_1$–$C_{12}$)alkyl and substituted phenyl($C_1$–$C_{12}$)alkyl, a group of formula H—[O(CH$_2$)$_m$]—n wherein m is the integer 2 or 3, n is an integer from 2 to 10 and one of the hydrogen atoms of a —CH$_2$— group may be substituted by a methyl group, a group of formula ($C_1$–$C_3$)alkyl[O(CH$_2$)$_m$]—n wherein m is the integer 2 or 3, n is an integer from 1 to 10 and one of the hydrogen atoms of a —CH$_2$— group may be substituted by a methyl group with the proviso that, in the case of alkyl esters, the proximal carbon on this alkyl chain must not be a tertiary carbon, which comprises r⒭acting a compound of formula

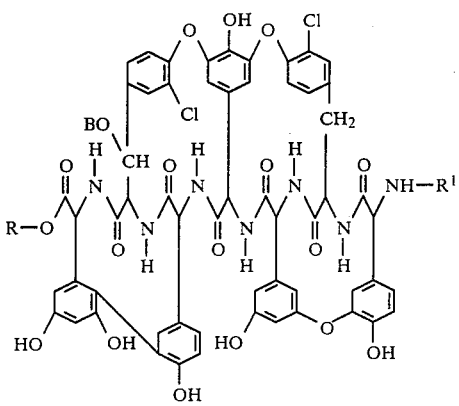

wherein R represents hydrogen, R$^1$ represents hydrogen or an amino protecting group, B represents an N-acetyl-β-D-glucosaminyl group with an excess of an alcohol of formula ROH wherein R is as defined above, in the presence of thionyl chloride at a temperature between −15° C. and room temperature.

* * * * *